United States Patent
Lee et al.

(10) Patent No.: US 10,687,741 B2
(45) Date of Patent: Jun. 23, 2020

(54) APPARATUS AND METHOD FOR MEASURING BIOLOGICAL COMPONENT

(71) Applicant: SAMSUNG ELECTRONICS CO., LTD., Suwon-si (KR)

(72) Inventors: So Young Lee, Daejeon (KR); Sang Kyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 504 days.

(21) Appl. No.: 15/581,189

(22) Filed: Apr. 28, 2017

(65) Prior Publication Data

US 2018/0116566 A1    May 3, 2018

(30) Foreign Application Priority Data

Nov. 3, 2016 (KR) .................. 10-2016-0145985

(51) Int. Cl.
- *A61B 5/1455* (2006.01)
- *A61B 5/00* (2006.01)
- *A61B 5/145* (2006.01)

(52) U.S. Cl.
CPC .......... *A61B 5/1455* (2013.01); *A61B 5/0075* (2013.01); *A61B 5/14532* (2013.01); *A61B 5/443* (2013.01); *A61B 5/7246* (2013.01)

(58) Field of Classification Search
CPC ..... A61B 5/1455; A61B 5/7246; A61B 5/443; A61B 5/14532; A61B 5/0075
See application file for complete search history.

(56) References Cited

U.S. PATENT DOCUMENTS

| | | |
|---|---|---|
| 5,028,787 A | 7/1991 | Rosenthal et al. |
| 5,068,536 A | 11/1991 | Rosenthal |
| 5,077,476 A | 12/1991 | Rosenthal |
| 5,086,229 A | 2/1992 | Rosenthal et al. |
| 5,204,532 A | 4/1993 | Rosenthal |
| 5,218,207 A | 6/1993 | Rosenthal |

(Continued)

FOREIGN PATENT DOCUMENTS

| | | |
|---|---|---|
| JP | 2000-60803 A | 2/2000 |
| JP | 2003-302406 A | 10/2003 |

(Continued)

OTHER PUBLICATIONS

Steven L Jacques., "Optical properties of biological tissues: a review", Topical Review, IOP Publishing, Institute of Physics and Engineering in Medicine, Physics in Medicine and Biology 58, (2013), (pp. R37-R61, 26 Pages Total) doi:10.1088/0031-9155/58/11/R37.

*Primary Examiner* — Eric F Winakur
*Assistant Examiner* — Abid A Mustansir
(74) *Attorney, Agent, or Firm* — Sughrue Mion, PLLC (57) ABSTRACT

An apparatus and method for measuring a biological component are provided. The apparatus may include a spectrum data acquirer configured to acquire spectrum data of a user by emitting light to a skin of the user and detecting the light reflected from the skin, and a processor configured to extract a user characteristic signal from the acquired spectrum data using a background signal and a first unit component spectrum and generate a second unit component spectrum personalized to the user by updating the first unit component spectrum based on the user characteristic signal.

20 Claims, 7 Drawing Sheets

(56) References Cited

U.S. PATENT DOCUMENTS

| | | |
|---|---|---|
| 5,237,178 A | 8/1993 | Rosenthal et al. |
| 5,362,966 A | 11/1994 | Rosenthal et al. |
| 5,365,066 A | 11/1994 | Krueger, Jr. et al. |
| 5,436,455 A | 7/1995 | Rosenthal et al. |
| 5,438,201 A | 8/1995 | Rosenthal et al. |
| 5,574,283 A | 11/1996 | Quintana |
| 5,576,544 A | 11/1996 | Rosenthal |
| 5,725,480 A * | 3/1998 | Oosta .................. A61B 5/0059 600/310 |
| 6,066,847 A | 5/2000 | Rosenthal |
| 7,041,468 B2 | 5/2006 | Drucker et al. |
| 7,460,895 B2 | 12/2008 | Arnold et al. |
| 8,140,139 B2 | 3/2012 | Grata et al. |
| 8,974,385 B2 | 3/2015 | Lee et al. |
| 9,037,206 B2 | 5/2015 | Grata et al. |
| 2005/0124868 A1 * | 6/2005 | Cho ........................ A61B 5/01 600/309 |
| 2006/0281982 A1 | 12/2006 | Grata et al. |
| 2007/0179367 A1 * | 8/2007 | Ruchti ............... A61B 5/14532 600/310 |
| 2010/0145173 A1 | 6/2010 | Alferness et al. |
| 2010/0312176 A1 | 12/2010 | Lauer et al. |
| 2016/0213290 A1 | 7/2016 | Park et al. |
| 2018/0020956 A1 | 1/2018 | Lee et al. |

FOREIGN PATENT DOCUMENTS

| | | |
|---|---|---|
| JP | 2008-5988 A | 1/2008 |
| JP | 2010-540133 A | 12/2010 |
| JP | 2014-211918 A | 11/2014 |
| KR | 10-1993-7001738 A | 6/1993 |
| KR | 10-2008-0026159 A | 3/2008 |
| KR | 10-2014-0094111 A | 7/2014 |
| KR | 10-1591072 B1 | 2/2016 |
| KR | 10-1632308 B1 | 6/2016 |
| KR | 10-2016-0090579 A | 8/2016 |
| KR | 10-2018-0011646 A | 2/2018 |

* cited by examiner

APPARATUS AND METHOD FOR MEASURING BIOLOGICAL COMPONENT

CROSS-REFERENCE TO RELATED APPLICATION

This application claims priority from Korean Patent Application No. 10-2016-0145985, filed on Nov. 3, 2016, in the Korean Intellectual Property Office, the entire disclosure of which is incorporated herein by reference.

BACKGROUND

1. Field

The following description relates to a technology for non-invasively measuring a biological component, and more specifically, to a technology for measuring a biological component using a personalized unit component spectrum.

2. Description of Related Art

Diabetes mellitus is a chronic disease which is difficult to treat and causes various complications, and hence a blood sugar level needs to be checked regularly to prevent any complications. When insulin is administered, blood sugar should be checked in order to prevent hypoglycemia and control the insulin dosage. Generally, measuring blood sugar requires an invasive method such as drawing blood with a finger prick. The method of measuring blood sugar in an invasive manner has high reliability of measurement, but the use of injection may cause pain during blood sampling, inconvenience, and a risk of infection. Recently, a method of non-invasive measurement of blood sugar using a spectrometer, without directly collecting blood, has been studied.

The method of measuring blood sugar using a spectrometer may estimate a variation of blood sugar using a background signal and a unit glucose spectrum $\varepsilon_{glucose}$ extracted from a glucose solution wherein the background signal is extracted from skin spectrum data when a blood sugar value is maintained at a constant value in a fasting state, and the method may predict a current blood sugar value by summing the fasting blood-sugar value and the variation of blood sugar.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, an apparatus for measuring a biological component may include: a spectrum data acquirer configured to acquire spectrum data of a user by emitting light to a skin of the user and detecting the light reflected from the skin; and a processor configured to extract a user characteristic signal from the acquired spectrum data using a background signal and a first unit component spectrum and generate a second unit component spectrum personalized to the user by updating the first unit component spectrum based on the user characteristic signal.

When the user characteristic signal is extracted, the processor may determine whether a personalization condition is satisfied based on the extracted user characteristic signal, and determine whether to update the first unit component spectrum based on a result of the determination of whether the personalization condition is satisfied.

When the result of determination indicates that the personalization condition is satisfied, the processor may determine that the first unit component spectrum is the personalized second unit component spectrum.

When the result of determination indicates that the personalization condition is not satisfied, the processor may perform preprocessing on the user characteristic signal and update the first unit component spectrum based on the preprocessed user characteristic signal.

When the first unit component spectrum is updated, the processor may re-extract a user characteristic signal from the acquired spectrum data based on the background signal and the updated first unit component spectrum, and determine whether the personalization condition is satisfied based on the re-extracted user characteristic signal.

The preprocessing may include a process of removing noise using at least one of a cosine value which determines a morphological similarity between the user characteristic signal and the first unit component spectrum, a correlation coefficient which determines linearity, a root means square (RMS) value which determines similarity, a Euclidean distance which determines a difference, and a t-test which determines similarity statistically.

The preprocessing may further include a process of smoothing the first unit component spectrum and the user characteristic signal from which the noise is removed.

The processor may update at least one of the background signal and the first unit component spectrum at a predetermined interval or upon request from the user.

The processor may measure biological component information which includes at least one of skin constituents and constituents of blood based on the generated second unit component spectrum.

The apparatus may further include an output unit configured to output, to the user, information including at least one of the first unit component spectrum, the second unit component spectrum, the background signal, the acquired spectrum, and a processing result of the processor.

According to an aspect of an exemplary embodiment, there is provided a method of measuring a biological component, the method including: acquiring spectrum data of a user by emitting light to a skin of the user and detecting the light reflected from the skin; extracting a user characteristic signal from the acquired spectrum data using a background signal and a first unit component spectrum; and generating a second unit component spectrum personalized to the user by updating the first unit component spectrum based on the user characteristic signal.

The generating the second unit component spectrum may include, in response to the user characteristic signal being extracted, determining whether a personalization condition is satisfied based on the extracted user characteristic signal, and determining whether to update the first unit component spectrum based on a result of the determination of whether the personalization condition is satisfied.

The generating of the second unit component spectrum may include determining that the first unit component spectrum is the personalized second unit component spectrum when a result of determination indicates that the personalization condition is satisfied.

The generating the second unit component spectrum may include preprocessing the user characteristic signal when the result of determination indicates that the personalization condition is not satisfied, and updating the first unit component spectrum based on the preprocessed user characteristic signal.

The generating the second unit component spectrum may include re-extracting a user characteristic signal from the acquired spectrum data based on the background signal and the updated first unit component spectrum when the first unit component spectrum is updated, and determining whether the personalization condition is satisfied based on the re-extracted user characteristic signal.

The preprocessing may include removing noise using at least one of a cosine value which determines a morphological similarity between the user characteristic signal and the first unit component spectrum, a correlation coefficient which determines linearity, a root means square (RMS) value which determines similarity, a Euclidean distance which determines a difference, and a t-test which determines similarity statistically.

The preprocessing may further include smoothing the first unit component spectrum and the user characteristic signal from which the noise is removed.

The method may further include updating at least one of the background signal and the first unit component spectrum at a predetermined interval or upon request from the user.

The method may further include measuring biological component information which includes at least one of skin constituents and constituents of blood based on the generated second unit component spectrum.

The method may further include outputting, to the user, information including at least one of the first unit component spectrum, the second unit component spectrum, the background signal, the acquired spectrum, and a processing result of the processor.

Other features and aspects will be apparent from the following detailed description, the drawings, and the claims.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

Hereinafter, various exemplary embodiments of an apparatus and method for measuring a biological component will be described with reference to the accompanying drawings.

Figure 1:
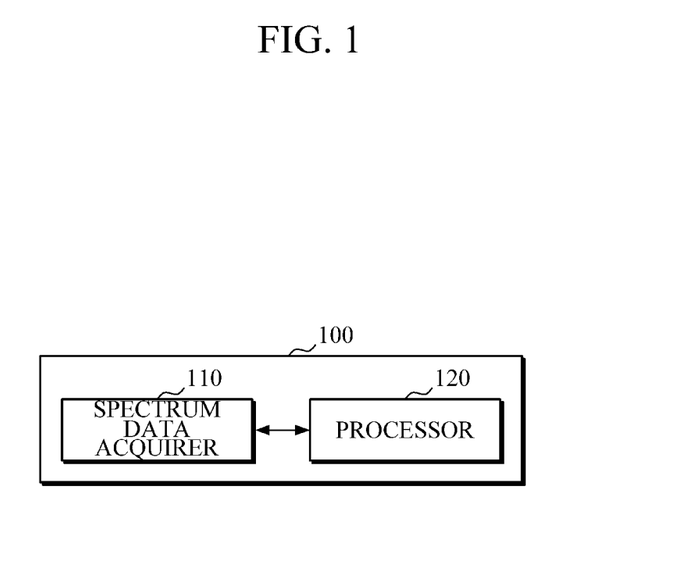
FIG. 1 is a block diagram illustrating an apparatus for measuring a biological component according to an exemplary embodiment.

FIG. 1 is a block diagram illustrating an apparatus for measuring a biological component according to an exemplary embodiment. The apparatus 100 for measuring a biological component may be an apparatus which non-invasively measures a biological component of a user by obtaining skin spectrum data of the user and personalizing a unit component spectrum.

Here, the biological component may be blood glucose of a user, which however is not limited thereto. The biological component may include skin constituents (e.g., protein, lipids, minerals, moisture, and the like), constituents of blood (e.g., triglycerides, cholesterol, blood cells, lactic acid, lithic acid, and the like), and components that constitute the human body. Hereinafter, however, for convenience of description, description will be given on the basis of an example in which the apparatus 100 measures blood glucose.

The apparatus 100 for measuring a biological component may be implemented as a software module and/or in the form of a hardware chip and mounted in an electronic device. In this case, the electronic device may include a mobile phone, a smart phone, a notebook computer, a personal digital assistant (PDA), a portable multimedia player (PMP), a navigation system, a digital music player (e.g., an MP3 player), a digital camera, a wearable device, etc. The wearable device may include various types of wearable devices, such as a wristwatch type, a wristband type, a ring type, a belt type, a necklace type, an ankle band type, a thigh band type, a forearm band type, and the like. However, the electronic device is not limited to the above mentioned examples, and the wearable device is also not limited to the above-described examples.

Referring to FIG. 1, the apparatus 100 includes a spectrum data acquirer 110 and a processor 120. In this case, the processor 120 may be configured with one or more processor, memories, and the combination thereof.

The spectrum data acquirer 110 may acquire user's spectrum data by emitting light to the user's skin and detecting light reflected from the skin. For example, the spectrum data acquirer 110 may include a light source which emits light in the near infrared ray (NIR) band or the middle infrared ray (MIR) band, a detector (e.g., a photo detector) including a photo diode, a photo transistor (PTr), or a charge-coupled device (CCD).

For example, when the user's blood glucose level is measured using the apparatus 100, the spectrum data acquirer 110 may emit light directly to the user's skin and acquire skin absorption spectrum data. In this case, the acquired spectrum data may be one or more spectrum data measured at the same measurement site over time.

In addition, the spectrum data acquirer 120 may be connected with an external spectrometer device over a wired/wireless network to acquire skin spectrum data from the external spectrometer device in real time or may receive skin spectrum data stored in the external storage device.

The processor 120 may extract a user characteristic signal using the acquired spectrum data, a background signal, and a first unit component spectrum. In this case, the background signal may be spectrum data measured at a predetermined time interval in a reference state (e.g., a fasting state) in which a change does not occur in a user's biological component, or may be in a processed form thereof. Here, the reference state may be set differently depending on the user's age, sex, skin condition, and biological component to be measured.

In addition, the first unit component spectrum may refer to a predetermined unit of spectrum of a biological component to be measured, and may serve as a reference unit component spectrum when a second unit component spectrum personalized to the user is generated, as described below.

Meanwhile, the background signal and the first unit component spectrum may be measured in advance before the measurement of biological component, but may not be limited thereto and may be acquired from the user in real time.

According to an aspect of an exemplary embodiment, the acquired spectrum data may be represented as an equation as shown in Equation 1. The processor 120 may extract a user characteristic signal using Equation 1. Equation 1 may be one example that represents skin spectrum data $S_t$ using unit glucose spectrum $\varepsilon_{glucose}$. Here, $S_t$ is a spectrum measured at time t, $B_v$ is the v-th loading vector extracted using at least one of principal component analysis (PCA), independent component analysis (ICA), and non-negative matrix factorization (NMF), $b_v$ is a coefficient of $B_v$ when interpretation is performed using a least squares method, and $b_v B_v$ may correspond to the background signal (e.g., any signals other than the one being monitored). In addition, $\varepsilon_{glucose}$ is a unit glucose spectrum, $L_t$ is an optical transmission path, $\Delta C_{pt}$ is a blood glucose change value measured at time t, and $\varepsilon_{glucose} \cdot L_t \cdot \Delta C_{pt}$ may correspond to a blood glucose signal extracted using the first unit glucose spectrum. Here, $\varepsilon_{glucose}$ may be an example of the first unit component spectrum. In addition, $e_t$ may be a signal other than the background signal and the blood glucose signal extracted using the first unit glucose spectrum, and may be remaining data or error data.

$$S_t = \Sigma_{v=1}^{k}(b_v B_v) + \varepsilon_{glucose} \cdot L_t \cdot \Delta C_{pt} + e_t \quad (1)$$

Thus, when there is little or no noise in the acquired spectrum $S_t$ or when the acquired spectrum $S_t$ fully corresponds to the background signal and the unit glucose spectrum $\varepsilon_{glucose}$ because the unit glucose spectrum $\varepsilon_{glucose}$ sufficiently reflects the user's personal characteristic, $e_t$ may converge to 0.

However, when the spectrum $S_t$ acquired using Equation 1 has a portion $e_t$ that does not correspond to the background signal or the unit glucose spectrum $\varepsilon_{glucose}$, the processor 120 may assume that portion $e_t$ is a signal that is attributable to the user's personal characteristic and may extract one or more $e_t$ values obtained for a predetermined period of time as user characteristic signal data. In this case, the extracted user characteristic signal data may be divided into a portion caused by the user's personal characteristic and a noise portion which is not associated with the user's personal characteristic, and the noise included in the user characteristic signal data $e_t$ may be removed through preprocessing.

As described above, the processor 120 may extract $e_t$ calculated from the spectrum data acquired using Equation 1 and the predetermined background signal and glucose signal as the user characteristic signal. Meanwhile, although Equation 1 is provided to describe a method of extracting the user characteristic signal according to an exemplary embodiment, the extraction of the user characteristic signal is not limited thereto.

When the user characteristic signal data is extracted, the processor 120 may update the first unit component spectrum using the extracted user characteristic signal data. For example, when the magnitude of the extracted user characteristic signal is equal to or greater than a predetermined level, it may indicate that the background signal and the first unit component spectrum by themselves do not sufficiently describe the acquired spectrum data. In this case, the processor 120 may update the first unit component spectrum by applying the portion caused by the user's personal characteristic, which is included in the user characteristic signal data, to the first unit component spectrum. For example, the processor 120 may update the unit glucose spectrum by calculating an average of the blood glucose signal data which includes the user characteristic signal data.

Meanwhile, the processor 120 may generate the second unit component spectrum personalized to the user using the first unit component spectrum. Here, the second unit component spectrum may be generated using the user characteristic signal data by adjusting the first unit component spectrum, and may be a personalized unit component spectrum to which the user characteristic information is applied.

Figure 2:
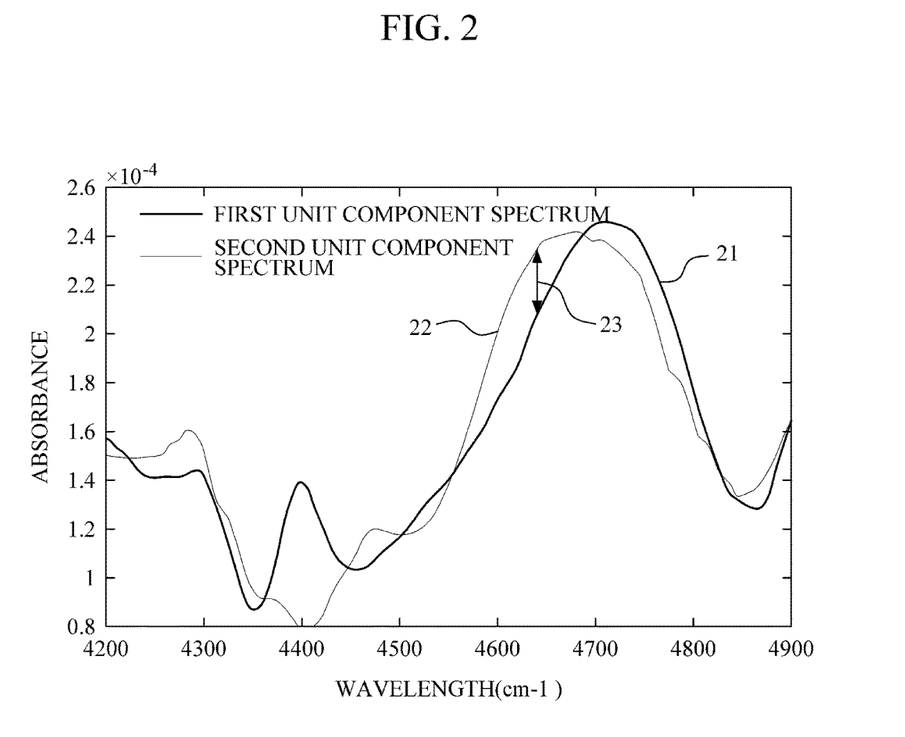
FIG. 2 is a graph showing a difference between the first unit component spectrum and the second component spectrum.

FIG. 2 is a graph showing a difference between the first unit component spectrum and the second component spectrum.

Referring to FIGS. 1 and 2, the first unit component spectrum 21 and the second unit component spectrum 22 may have a difference 23. For example, when the first unit component spectrum 21 is an already-known unit glucose component spectrum, the apparatus 100 for measuring a biological component may generate the second unit component spectrum 22 personalized to the user using the user characteristic signal data by applying the remaining data of the acquired spectrum data which is not attributable to the background signal or the unit glucose component spectrum to the second unit component spectrum 22. In this case, the difference 23 may be caused by the user characteristic signal.

In addition, although FIG. 2 illustrates the user characteristic signal-based difference between the first unit component spectrum 21 and the second unit component spectrum 22, when the user characteristic signal extracted from the acquired spectrum data using the first unit component spectrum 21 satisfies a personalization condition, the first unit component spectrum and the second unit component spectrum may be identical to each other, and in this case, the difference 23 may not exist.

Figure 3:
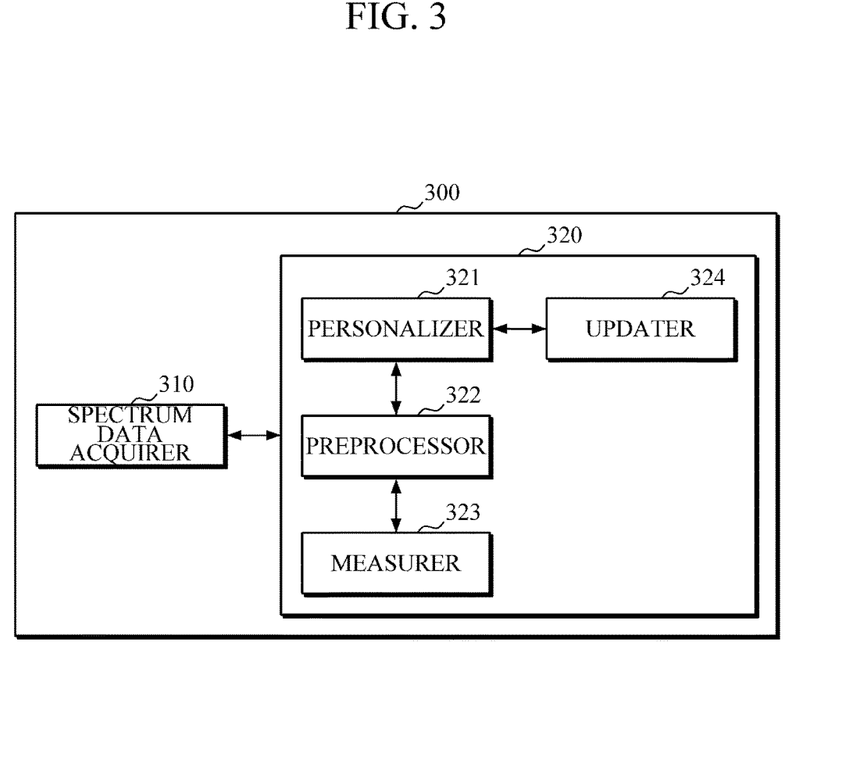
FIG. 3 is a block diagram illustrating a processor of an apparatus for measuring a biological component according to another exemplary embodiment.

FIG. 3 is a block diagram illustrating a processor of an apparatus for measuring a biological component according to another exemplary embodiment. Referring to FIG. 3, the apparatus 300 includes a spectrum data acquirer 310 and a processor 320. The processor 320 may further include a personalizer 321, a preprocessor 322, a measurer 323, and an updater 324. In this case, the processor 320 may be one example of the processor 120 shown in FIG. 1. Each component shown in FIG. 3 may be implemented with software, hardware, or a combination thereof.

The personalizer 321 may extract user characteristic signal data from an acquired spectrum data of a user. For example, the personalizer 321 may assume and extract a portion of the acquired spectrum data which is not attributable to a background signal or a first unit component spectrum as a user characteristic signal. The personalizer 321 may determine whether the personalized condition is satisfied or not on the basis of the extracted user characteristic signal. In this case, the personalization condition may mean whether a value of the extracted user characteristic signal stays below the threshold value when the value is compared with the threshold value.

For example, when the extracted user characteristic signal exceeds the predetermined threshold, it may indicate that the background signal and the first unit component spectrum alone do not sufficiently account for the acquired spectrum data, and the personalizer 321 may compare the user characteristic signal with the threshold value in order to determine whether to update the first unit component spectrum and determine whether the personalization condition is satisfied on the basis of the comparison result.

In addition, the personalizer 321 may compare an average value of the user characteristic signal data extracted from one or more spectrum data obtained from the user's skin with the predefined threshold value and determine whether the personalization condition is satisfied. In this case, the acquired spectrum data may be a set of spectra continuously obtained at the same position of the skin at different times. In addition, aspects of the present disclosure are not limited to the above example, and the personalizer 321 may compare the average value, variance, or standard deviation of the user characteristic signal data with the predefined threshold value to determine whether the personalization condition is satisfied. That is, whether the personalization condition is satisfied or not may indicate how well the acquired spectrum data is described by (e.g., correspond to) the background signal and the first unit component spectrum.

The personalizer 321 may determine whether to update the first unit component spectrum according to the result of determination on whether the personalization condition is satisfied. For example, when the user characteristic signal extracted from the acquired spectrum satisfies the personalization condition, it may indicate that the background signal and the first unit component spectrum well describe the acquired spectrum, and the personalizer 321 may determine that the first unit component data does not need to be updated.

Meanwhile, when the result of comparison between the user characteristic signal and the threshold value indicates that the personalization condition is not satisfied, it may indicate that the acquired spectrum is not sufficiently described by the background signal and the first unit component spectrum, and at this time, the personalizer 321 may determine to update the first unit component spectrum.

According to one embodiment, the personalizer 321 may update the first unit component spectrum through Equation 2. Here, $L_t$ is an optical transmission path at time t, $\Delta C_{pt}$ is a blood glucose change value prediction at time t, $\Delta C_t$ is an actual blood glucose change value at time t, $\varepsilon_{glucose}$ is a unit glucose spectrum, $\varepsilon_{glucose}'$ is an updated unit glucose spectrum, and $e_t$ is remaining data or error data that does not correspond to either the background signal or the biological component signal and may be user characteristic signal data. In addition, when it is not possible to determine a value of $\Delta C_t$, $\Delta C_{pt}$ may be substituted instead. In addition, $\varepsilon_{glucose}$ may be one example of the first unit component spectrum.

$$\varepsilon_{glucose}' = \frac{\sum_{t=t1}^{tN} \varepsilon_{glucose} \cdot L_t \cdot \Delta C_{pt} + e_t}{\sum_{t=t1}^{tN} L_t \cdot \Delta C_t} \tag{2}$$

That is, the personalizer 321 may update the unit glucose spectrum using an average of data obtained by summing a blood glucose signal $\varepsilon_{glucose} \cdot L_t \cdot \Delta C_{pt}$ represented as a unit glucose spectrum and the user characteristic signal $e_t$ which are in the spectrum data acquired at the same position for a period from t1 to tN.

Equation 2 is one example of updating the first unit component spectrum, and the update of the first unit component spectrum is not limited thereto. For example, the personalizer 321 may update the first unit component spectrum using a weight average value obtained by applying a weight to a predetermined spectral region of the user characteristic signal data.

Meanwhile, when the first unit component spectrum is updated, the personalizer 321 may re-extract the user characteristic signal on the basis of the first unit component spectrum and the background signal. For example, when the re-calculated user characteristic signal on the basis of the background signal and the updated first unit component spectrum does not satisfy the personalization condition, the personalizer 321 may repeat the update of the first unit component spectrum until the user characteristic signal satisfies the personalization condition.

For example, when the first user characteristic signal has been extracted on the basis of the first unit component spectrum and the first user characteristic signal does not satisfy the personalization condition, the first unit component spectrum may be updated based on the first user characteristic signal, and the second user characteristic signal may be extracted based on the updated first unit component spectrum. In this case, the personalizer 321 may re-perform a process of determining whether the personalization condition is satisfied on the basis of the second user characteristic signal, and when the second user characteristic signal does not satisfy the personalization condition, the personalizer 321 may re-update the updated first unit component spectrum on the basis of the second user characteristic signal.

As described above, the personalizer 321 may repeatedly perform processes of updating the first unit component spectrum, re-extracting a user characteristic signal on the basis of the first unit component spectrum and the background signal, and determining whether the personalization condition is satisfied on the basis of the extracted user characteristic signal. The first unit component spectrum is gradually personalized through the repeated processes as described above, and the number of repetitions may be set in advance.

When the user characteristic signal extracted based on the updated first unit component spectrum and the background signal satisfies the personalization condition, the personalizer 321 may determine that the first unit component spectrum sufficiently reflects the user's personal characteristic, and may determine that the updated first unit component spectrum is a second unit component spectrum.

When the first unit component spectrum is determined to be updated, the preprocessor 322 may remove noise by preprocessing the user characteristic signal data. For example, as described above, the user characteristic signal may include feature information which is presented according to the user's physical characteristics, such as the user's race, age, and sex, and a change in biological component, and the user's skin condition, and noise which is caused by a non-biological component. In addition, referring to Equation 2, since the first unit component spectrum may be updated using biological component data (e.g., blood glucose signal data) including the user characteristic signal $e_t$, the preprocessor 322 may remove the noise which is not caused by the biological component and provide only the feature information that is presented in the user characteristic signal data $e_t$ according to the user's physical characteristics to the personalizer 321.

For example, the preprocessor 322 may remove the noise from the user characteristic signal data through the morphological similarity, difference, and statistical test between the first unit component spectrum and the user characteristic signal. For example, the preprocessor 322 may remove the noise from the user characteristic signal data by normalizing the first unit component spectrum and the user characteristic signal and applying a cosine filter on the basis of the morphological similarity between the first unit component spectrum and the user characteristic signal. In addition, the preprocessor 320 may remove the noise caused by a non-biological component using at least one of a pulse shaping filter, a correlation coefficient that determines the linearity between the user characteristic signal and the first unit component spectrum, a root means square (RMS) value which determines the similarity, a Euclidean distance which determines the difference, and the t-test which determines the similarity statistically. In addition, the preprocessor 320 may smooth the updated first unit spectrum and/or the user characteristic signal from which the noise has been removed using at least one of preprocessing filters including a moving average filter, an average value filter, and a Gaussian filter.

As such, the preprocessor 322 may update the first unit component spectrum using the user characteristic signal data which includes only the feature information that is presented according to the user's physical characteristics by removing the noise caused by a non-biological component from the user characteristic signal data. The measurer 323 may measure the biological component information which includes at least one of skin constituents and constituents of blood on the basis of the generated second unit component spectrum. For example, when the apparatus 300 measures the user's blood glucose level, the measurer 323 may measure the user's biological component information from the acquired spectrum using the predetermined background signal and the first unit component spectrum (e.g., a unit glucose spectrum), and may accurately measure the user's blood glucose level using the second unit component spectrum (e.g., a unit glucose spectrum individually personalized) personalized to the user on the basis of the user characteristic signal.

The updater 324 may update one or both of the background signal and the first unit component spectrum at a predetermined interval or in response to a user's request. In this case, the predetermined interval may be a unit time, a day, a week, a month, or an arbitrary period of time. For example, referring to FIGS. 1 and 3, assuming that the apparatus 100 for measuring a biological component is mounted in a wearable device, the apparatus 100 in the wearable device may change the position at which to acquire the spectrum data according to the movement of the user and the user characteristic signal data may vary depending on the change in a biological component of the user (e.g., an increase in subcutaneous fat), skin aging or damage, or the like. In this case, the updater 324 may provide the personalizer 321 with data for accurately measuring the biological component regardless of a change in the position where the spectrum is acquired or the change in the biological component of the user by updating one or both of the background signal and the first unit component spectrum at the predetermined interval or in response to a update request instruction from the user.

That is, the updater 324 may update the background signal and the first unit component spectrum when measuring the biological component, and may independently update the background signal and the first unit spectrum, in advance, periodically or upon request from the user.

Figure 4:
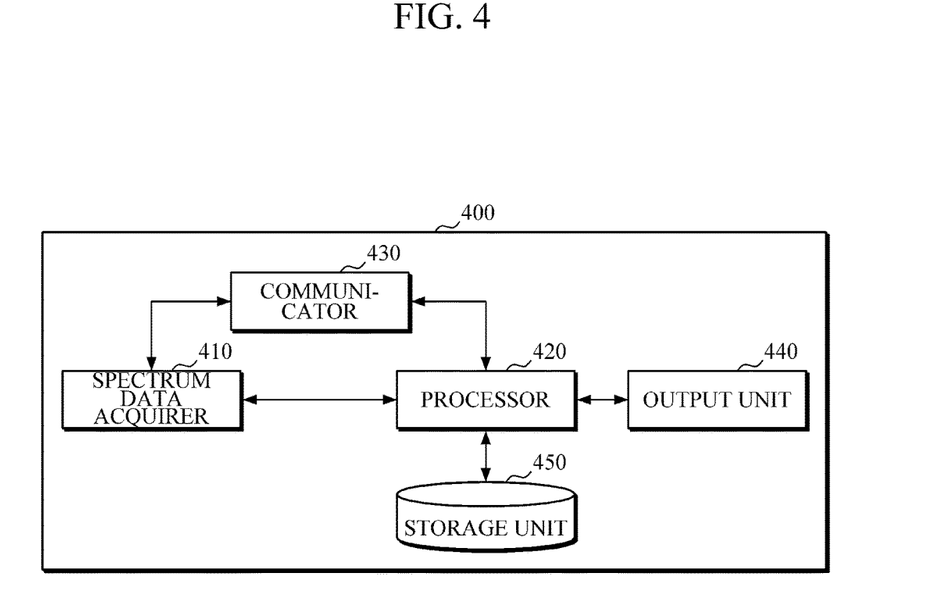
FIG. 4 is a block diagram illustrating an apparatus for measuring a biological component according to another exemplary embodiment.

FIG. 4 is a block diagram illustrating an apparatus for measuring a biological component according to another exemplary embodiment. Referring to FIG. 4, an apparatus 400 for measuring a biological component includes a spectrum data acquirer 410, a processor 420, a communicator 430, an output unit 440, and a storage unit 450. In this case, the spectrum data acquirer 410 and the processor 420 may be configured to be substantially the same as the spectrum data acquirer 110 and the processor 120 of FIG. 1 and the processor 300 of FIG. 3, and hereinafter, a description in detail will be given, focusing on components that are not redundant.

The communicator 430 may be connected with an external spectrometer device over a wired/wireless network to acquire skin spectrum data from the external spectrometer device in real time or may receive skin spectrum data stored in the external storage device. For example, the communicator 430 may acquire the user's spectrum data by accessing the external device in response to a control instruction from the processor 420, and may transmit measured biological component information of the user to the external device.

In this case, the external device may be medical equipment that uses measured biometric component information, a printer for outputting a result, or a display device to display estimated skin condition information. Additionally, the external device may be a digital TV, a desktop computer, a mobile phone, a smart phone, a tablet computer, a notebook computer, a personal digital assistant (PDA), a portable multimedia player, a navigation system, an MP3 player, a digital camera, a wearable device, and an electronic device for processing digital signals, but is not limited thereto.

In addition, the communicator 430 may include one or more modules for communicating via Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like.

The output unit 440 may output various types of information including a first unit spectrum, a second unit spectrum, a background signal, the acquired spectrum, and a result of the processor, to the user. For example, the output unit 440 may be a touchscreen display which displays the background signal and the first unit spectrum in different sections and includes a user interface (UI) that displays an update history and details of each of the background signal and the first unit spectrum. However, the output unit 440 is not limited to the above examples, and may use a non-visual output method, such as an audible method (e.g., voice alarm, etc.) or a tactile method (e.g., vibration, etc.).

The storage unit 450 may store the spectrum data, the background signal, the first unit component spectrum, the second unit component spectrum, biological component information, user personal information and a variety of information. For example, the storage unit 450 may store the background signal and the first unit component spectrum in a reference data category, and store the updated data in a separate category. In addition, the storage unit 450 may manage a change trend according to the number of updates of the background signal and the first unit spectrum for the same user. The storage unit 450 may also store any instructions (e.g., code, program instructions, application programming interface, etc.) which, when executed by the processor 420, may cause the processor 420 to perform various operations and functions as described herein.

In this case, the storage unit 450 may include a flash memory, a hard disk, a micro type multimedia card, and a card type memory (e.g., SD or XD memory), a random access memory (RAM), a static random access memory (SRAM), a read-only memory (ROM), an electrically erasable programmable read only memory (EEPROM), a programmable read only memory (PROM), a magnetic memory, a magnetic disk, and an optical disk, but is not limited thereto.

Figure 5:
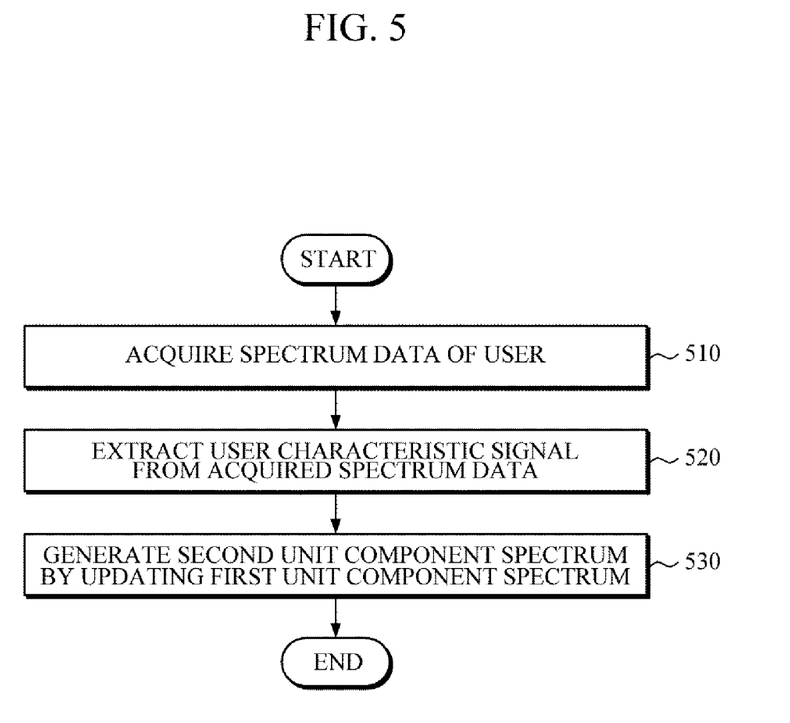
FIG. 5 is a flowchart illustrating a method of measuring a biological component according to an exemplary embodiment.

FIG. 5 is a flowchart illustrating a method of measuring a biological component according to an exemplary embodiment. The method shown in FIG. 5 may correspond to an exemplary method performed by the apparatus 100 of FIG. 1 to measure a biological component.

Referring to FIGS. 1 and 5, the apparatus 100 for measuring a biological component acquires spectrum data about the user's skin by emitting light to the user's skin and detecting light reflected from the skin (510). In this case, the apparatus 100 may include a spectrometer and a detector to directly emit light to the user's skin and acquire skip absorption spectrum data. In addition, the apparatus 100 may acquire the user's spectrum data through an external apparatus for measuring a biological component or a biological component management server in which the user's spectrum data is stored.

The apparatus 100 may extract a user characteristic signal using the acquired spectrum data, a background signal, and a first unit component spectrum (520). In this case, the background signal may be spectrum data measured at a predetermined time interval in a reference state (e.g., fasting state) in which a change does not occur in a user's biological component, or may be in a processed form thereof. Here, the reference state may be set differently depending on the user's age, sex, skin condition, and biological component to be measured.

The first unit component spectrum may serve as a reference unit component spectrum when a second unit component spectrum personalized to the user is generated (530), as described below, and it may be defined in advance. In addition, aspects of the present disclosure are not limited to the above description, and the apparatus 100 may acquire the background signal and the first unit component spectrum from the user in real time when measuring the biological component.

The apparatus 100 extracts a user characteristic signal from data which is not accounted for by the background signal and the first unit component spectrum in the acquired spectrum data (520). For example, the acquired skin spectrum may be represented as the background signal and the first unit component spectrum, as shown in Equation 1, and the apparatus 100 may assume that the remaining data which is not reflected in the background signal and the first unit component spectrum is caused by the user's characteristic, and the apparatus 100 may extract the user characteristic signal from the remaining data.

When the user characteristic signal data is extracted, the apparatus 100 generates a second unit component spectrum by updating the first unit component spectrum (530). For example, the apparatus 100 may update the first unit component spectrum using an average value of the biological component data including the user characteristic signal data and generate the second unit component spectrum by determining that the updated first unit component spectrum is the second unit component spectrum personalized to the user.

Figure 6:
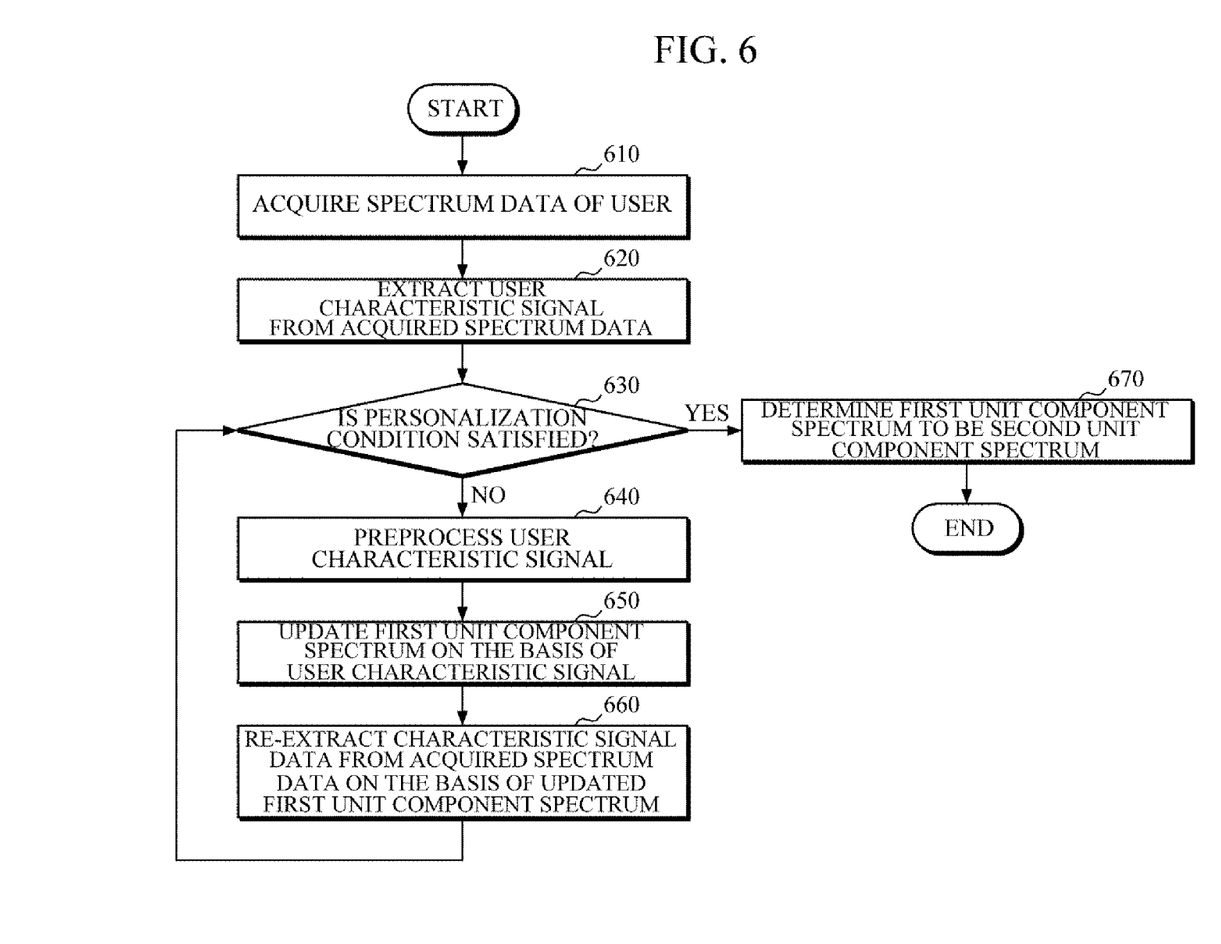
FIG. 6 is a flowchart illustrating a method of measuring a biological component according to another exemplary embodiment.

FIG. 6 is a flowchart illustrating a method of measuring a biological component according to another exemplary embodiment. The method shown in FIG. 6 may correspond to an exemplary method performed by the apparatus 100 of FIG. 1 or the apparatus 300 of FIG. 3 to measure a biological component.

Referring to FIGS. 3 and 6, the apparatus 300 for measuring a biological component acquires spectrum data of the user by emitting light to the user's skin and detecting light reflected from the skin (610).

When the spectrum data of the user is acquired, the apparatus 300 extracts user characteristic signal data from the acquired user characteristic signal data using a background signal and a first unit component spectrum (620). Here, the user characteristic signal data may be remaining data or error data which is not reflected in (e.g., accounted for by) the background signal and the first unit component spectrum in the acquired spectrum data.

The apparatus 300 determines whether a personalization condition is satisfied using the extracted user characteristic signal (630). Here, satisfying the personalization condition may mean that a value of the extracted user characteristic signal stays below a threshold value. For example, the apparatus 300 may compare the average value, variance, or standard deviation of the extracted user characteristic signal data with the predetermined threshold value. When the average value, variance or standard deviation of the extracted user characteristic signal data exceeds the threshold value, the apparatus 300 may determine that the personalization condition is not satisfied, and when the value is less than or equal to the threshold value, may determine that the personalization condition is satisfied.

When the user characteristic signal does not satisfy the personalization condition, it may indicate that the first unit component spectrum may not sufficiently reflect the user's characteristic, and the apparatus 300 preprocesses the user characteristic signal data before updating the first unit component spectrum on the basis of the user characteristic signal data (640).

For example, the user characteristic signal data extracted by the apparatus 300 may include feature information which is presented according to the user's physical characteristics, such as the user's race, age, and sex, and a change in biological component, and the user's skin condition, and noise which is caused by a non-biological component. The apparatus 300 may remove the noise which is caused by a non-biological component from the user characteristic signal data.

For example, the apparatus 300 may remove the noise from the user characteristic signal data using a pulse shaping filter on the basis of a similarity between the first unit component spectrum and the user characteristic signal or using a correlation coefficient which determines the linearity between the acquired spectrum and the first unit component spectrum. In addition, the apparatus 300 may remove the noise from the user characteristic signal data using an RMS value or a Euclidean distance on the basis of the similarity between the first unit component spectrum and the user characteristic signal, but is not limited thereto, and may remove the noise through a statistical test, such as a t-test which determines the similarity statistically, between the first unit component spectrum and the user characteristic signal. However, these are merely examples and various preprocessing methods for removing the noise which is caused by non-biological information of the user from the user characteristic signal data may be applied.

In another example, the apparatus 300 may smooth the updated first unit component spectrum and/or the user characteristic signal from which the noise has been removed using at least one of preprocessing filters including a moving average filter, an average value filter, and a Gaussian filter.

The apparatus 300 updates the first unit component spectrum using the preprocessed user characteristic signal data (650). For example, referring to Equation 1 and Equation 2, the acquired spectrum may include the biological component signal $\varepsilon_{glucose} \cdot L_t \cdot \Delta C_{pt}$ and the user characteristic signal $e_t$. In this case, the apparatus 300 may update the first unit component spectrum by calculating an average of the biological component data including the user characteristic signal data.

Meanwhile, referring to FIG. 6, it is illustrated that operation 640 of preprocessing the user characteristic signal data is performed before operation 650 of updating the first unit component spectrum, which is merely an example, and the preprocessing operation may be performed on the first unit component spectrum after updating the first unit component spectrum.

When the first unit component spectrum is updated, the apparatus 300 re-extracts the user characteristic signal data from the acquired spectrum data using the updated first unit component spectrum (660). The apparatus 300 may repeat the above operations until the re-extracted user characteristic signal data satisfies the personalization condition. As such, by repeatedly performing the update of the first unit component spectrum and determination on whether the personalization condition is satisfied, it is possible to generate a second unit component spectrum which sufficiently reflects the user's characteristic may be generated. The first unit component spectrum is gradually personalized through the repeated processes as described above, and the number of repetitions may be set in advance.

When the extracted user characteristic signal data satisfies the personalization condition, the apparatus 300 generates the second unit component spectrum by determining that the updated first unit component spectrum is the second unit component spectrum (670). That is, the second unit component spectrum may be a unit component spectrum which reflects the user's personal characteristic on the first unit component spectrum on the basis of the user characteristic signal data.

Figure 7:
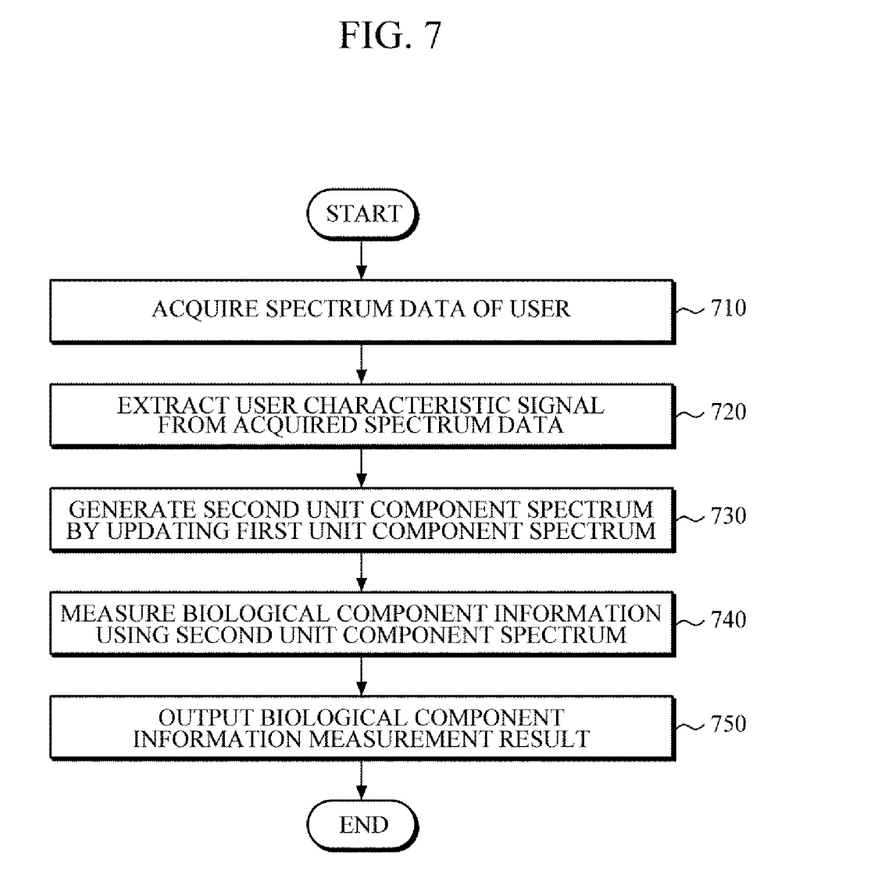
FIG. 7 is a flowchart illustrating a method of measuring a biological component according to another exemplary embodiment.

FIG. 7 is a flowchart illustrating a method of measuring a biological component according to another embodiment. The method shown in FIG. 7 may correspond to a method performed by the apparatus 100, 300, or 400 of FIG. 1, 3, or 4 to measure a biological component.

Referring to FIGS. 4 and 7, the apparatus 400 for measuring a biological component acquires a skin spectrum of a user by emitting light to the user's skin and detecting light reflected from the skin (710), and extracts a user characteristic signal from the acquired spectrum using a background signal and a first unit component spectrum (720). Here, the user characteristic signal data may be data which is not reflected in (e.g., accounted for by) the background signal and the first unit component spectrum in the acquired spectrum data.

When the user characteristic signal data is extracted, the apparatus 400 generates a second unit component spectrum by updating the first unit component spectrum (730). For example, the apparatus 400 may update the first unit component spectrum by calculating an average of the biological component data including the user characteristic signal data, and may generate the second unit component spectrum by determining that the updated first unit component spectrum is the second unit component spectrum.

The apparatus 400 measures biological component information of the user using the second unit component spectrum (740). For example, if the user's spectrum acquired in 710 is a skin spectrum acquired to measure a user's blood glucose level, the apparatus 400 may measure the user's blood glucose level from the acquired skin spectrum using the background signal and the second unit component spectrum, so that an accurate measurement result which reflects the user's personal characteristics (e.g., race, age, sex, a change in biological component, user's skin condition, etc.) can be obtained.

When the biological component information of the user is measured, the apparatus 400 outputs the measurement result (750). For example, the apparatus 400 may output a variety of information including the first unit component spectrum, the second unit component spectrum, the background signal, the acquired spectrum, and the result from the processor to the user.

For example, the apparatus 400 may displays the background signal and the first unit spectrum in different sections on a touchable display and may also display UI that displays an update history and details of each of the background signal and the first unit spectrum. However, aspects of the present disclosure are not limited to the above example, and the apparatus 400 may use a non-visual output method, such as an audible method (e.g., voice alarm, etc.) or a tactile method (e.g., vibration, etc.).

In addition, the apparatus 400 may store a variety of information including the acquired spectrum, the background signal, the first unit component spectrum, the second unit component spectrum, biological component information, user's personal information, and the measurement result of the apparatus 400.

After generating the second unit component spectrum by updating the first unit component spectrum, the apparatus 400 may update one or both of the background signal and the first unit component spectrum at a predetermined interval or upon request from the user. That is, in addition to the case of generating the second unit component spectrum for measuring the biological component, the apparatus 400 may re-acquire the spectrum data of the user at a predetermined interval or in response to an update instruction from the user and generate the second unit component spectrum on the basis of the re-acquired spectrum data.

According to the periodic update as described above, the apparatus may output an accurate biological component measurement result without a delay in response to an instruction to measure a biological component of the user.

The current embodiments can be implemented as computer-readable instructions or code in a computer-readable storage medium. The computer-readable storage medium includes all types of storage media in which computer-readable data are stored. Examples of the computer-readable storage medium include a ROM, a RAM, a compact disc ROM (CD-ROM), a magnetic tape, a floppy disk, and an optical data storage. In addition, the computer-readable storage medium may be distributed among computer systems over a network, in which computer-readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for measuring a biological component, the apparatus comprising:
   a spectrum data acquirer configured to acquire spectrum data of a user by emitting light to a skin of the user and detecting the light that is reflected from the skin; and
   a processor configured to:
      extract a user characteristic signal from the acquired spectrum data by subtracting, from the acquired spectrum data, a background signal and a first unit component spectrum, the background signal being spectrum data that is measured at a predetermined time interval in a reference state in which a change does not occur in the biological component, and the first unit component spectrum being a predetermined unit of spectrum of the biological component; and
      obtain a second unit component spectrum that is personalized to the user by updating the first unit component spectrum based on the extracted user characteristic signal.

2. The apparatus of claim 1, wherein the processor is further configured to:
   determine whether the extracted user characteristic signal is greater than a predetermined threshold; and
   based on the extracted user characteristic signal being determined to be greater than the predetermined threshold, determine to update the first unit component spectrum.

3. The apparatus of claim 2, wherein the processor is further configured to, based on the extracted user characteristic signal being determined to be less than or equal to the predetermined threshold, determine that the first unit component spectrum is the personalized second unit component spectrum.

4. The apparatus of claim 2, wherein the processor is further configured to:
   based on the extracted user characteristic signal being determined to be greater than the predetermined threshold, preprocess the extracted user characteristic signal; and
   update the first unit component spectrum based on the preprocessed user characteristic signal.

5. The apparatus of claim 4, wherein the processor is further configured to, based on the first unit component spectrum being updated, re-extract the user characteristic signal from the acquired spectrum data by subtracting, from the acquired spectrum data, the background signal and the updated first unit component spectrum; and
   determine whether the re-extracted user characteristic signal is greater than the predetermined threshold.

6. The apparatus of claim 4, wherein the processor is further configured to remove noise from the extracted user characteristic signal, using any one or any combination of a cosine value that determines a morphological similarity between the extracted user characteristic signal and the first unit component spectrum, a correlation coefficient that determines linearity, a root means square (RMS) value that determines similarity, a Euclidean distance that determines a difference, and a t-test that determines similarity statistically.

7. The apparatus of claim 6, wherein the processor is further configured to smooth the first unit component spectrum and the user characteristic signal from which the noise is removed.

8. The apparatus of claim 1, wherein the processor is further configured to update either one or both of the background signal and the first unit component spectrum at the predetermined interval or upon request from the user.

9. The apparatus of claim 1, wherein the processor is further configured to measure biological component information that includes either one or both of skin constituents and constituents of blood, based on the obtained second unit component spectrum.

10. The apparatus of claim 1, further comprising a display configured to display, to the user, information including any one or any combination of the first unit component spectrum, the obtained second unit component spectrum, the background signal, the acquired spectrum data, and a processing result of the processor.

11. A method of measuring a biological component, the method comprising:
   acquiring spectrum data of a user by emitting light to a skin of the user and detecting the light that is reflected from the skin;
   extracting a user characteristic signal from the acquired spectrum data by subtracting, from the acquired spectrum data, a background signal and a first unit component spectrum, the background signal being spectrum data that is measured at a predetermined time interval in a reference state in which a change does not occur in the biological component, and the first unit component spectrum being a predetermined unit of spectrum of the biological component; and
   obtaining a second unit component spectrum that is personalized to the user by updating the first unit component spectrum based on the extracted user characteristic signal.

12. The method of claim 11, wherein the obtaining the second unit component spectrum comprises:
   determining whether the extracted user characteristic signal is greater than a predetermined threshold; and based on the extracted user characteristic signal being determined to be greater than the predetermined threshold, determining to update the first unit component spectrum.

13. The method of claim 12, wherein the obtaining the second unit component spectrum further comprises, based on the extracted user characteristic signal being determined to be less than or equal to the predetermined threshold, determining that the first unit component spectrum is the personalized second unit component spectrum.

14. The method of claim 12, wherein the obtaining the second unit component spectrum further comprises:
based on the extracted user characteristic signal being determined to be greater than the predetermined threshold, preprocessing the extracted user characteristic signal; and
updating the first unit component spectrum based on the preprocessed user characteristic signal.

15. The method of claim 14, wherein the obtaining the second unit component spectrum further comprises:
based on the first unit component spectrum being updated, re-extracting the user characteristic signal from the acquired spectrum data by subtracting, from the acquired spectrum data, the background signal and the updated first unit component spectrum in response to the first unit component spectrum being updated; and
determining whether the re-extracted user characteristic signal is greater than the predetermined threshold.

16. The method of claim 14, wherein the preprocessing comprises removing noise from the extracted user characteristic signal, using any one or any combination of a cosine value that determines a morphological similarity between the extracted user characteristic signal and the first unit component spectrum, a correlation coefficient that determines linearity, a root means square (RMS) value that determines similarity, a Euclidean distance that determines a difference, and a t-test that determines similarity statistically.

17. The method of claim 16, wherein the preprocessing further comprises smoothing the first unit component spectrum and the user characteristic signal from which the noise is removed.

18. The method of claim 11, further comprising updating either one or both of the background signal and the first unit component spectrum at the predetermined interval or upon request from the user.

19. The method of claim 11, further comprising measuring biological component information that includes either one or both of skin constituents and constituents of blood, based on the obtained second unit component spectrum.

20. The method of claim 11, further comprising displaying, to the user, information including any one or any combination of the first unit component spectrum, the obtained second unit component spectrum, the background signal, the acquired spectrum data, and a processing result.

* * * * *